United States Patent [19]

Webb

[11] Patent Number: 4,758,267

[45] Date of Patent: Jul. 19, 1988

[54] ULTRAFINE PARTICLE AND FIBER PRODUCTION IN MICROGRAVITY

[75] Inventor: George W. Webb, Del Mar, Calif.

[73] Assignee: Energy Science Laboratories, Inc., San Diego, Calif.

[21] Appl. No.: 811,992

[22] Filed: Dec. 23, 1985

[51] Int. Cl.$^4$ .............................................. B22F 9/00
[52] U.S. Cl. ............................ 75/0.5 B; 156/DIG. 62
[58] Field of Search ............. 75/0.5 R, 0.5 B, 0.5 BB, 75/0.5 BA; 156/DIG. 62; 266/200, 202, 217; 65/21.4, 22; 204/164

[56] References Cited

U.S. PATENT DOCUMENTS

| | | | |
|---|---|---|---|
| 4,279,632 | 7/1981 | Frosch et al. | 65/21.4 |
| 4,385,080 | 5/1983 | de Rudnay | 156/DIG. 62 |
| 4,556,416 | 12/1985 | Kamijo et al. | 75/0.5 B |

FOREIGN PATENT DOCUMENTS

0702612  1/1965  Canada ................................ 75/0.5 B

OTHER PUBLICATIONS

Margrave et al., "The Use of Levitation in Inorganic Synthesis" *High Temperature Science*, vol. 3, No. 2, pp. 163-167, 12/71.

NASA Publication: *Microgravity Science and Applications*, pp. 1-55, 12/84.

Kimoto et al., "An Electron Microscope Study on Fine Metal Particles Prepared by Evaporation in Argon Gas at Low Pressure", Japan. J. Appl. Phys., vol. 2, No. 11, Nov. 1963, pp. 702-713.

Tasaki et al., "Magnetic Properties of Ferromagnetic Metal Fine Particles Prepared by Evaporation in Argon Gas", Japan. J. Appl. Phys., vol. 4, No. 10, Oct. 1965, pp. 707-711.

Kimoto and Nishida, "An Electron Microscope and Electron Diffraction Study of Fine Smoke Particles Prepared by Evaporation in Argon Gas at Low Pressures (II)", Japan. J. Appl. Phys., vol. 6, No. 9, Sep. 1967, pp. 1047-1059.

Yatsuya et al., "Formation of Ultrafine Metal Particles by Gas Evaporation Technique. I. Aluminum in Helium", Japan. J. Appl. Phys., vol. 12, No. 11, Nov. 1973, pp. 1675-1684.

Wada and Ichikawa, "A Method of Preparation of Finely Dispersed Ultrafine Particles", Japan. J. Appl. Phys., vol. 15, No. 5, May 1976, pp. 755-756.

Kato, "Preparation of Ultrafine Particles of Refractory Oxides by Gas-Evaporation Method", Japan. J. Appl. Phys., vol. 15, No. 5, May 1976, pp. 757-760.

Granqvist and Buhrman, "Ultrafine Metal Particles", J. Appl. Phys., vol. 47, No. 5, May 1976, pp. 2200-2219.

Kaito et al., "Growth of CdS Smoke Particles Prepared by Evaporation in Inert Gases", J. Appl. Phys., vol. 47, No. 12, Dec. 1976, pp. 5161-5166.

Hayashi et al., "Formation of Ultrafine Metal Particles by Gas-Evaporation Technique. IV. Crystal Habits of Iron and Fcc Metals, Al, Co, Ni, Cu, Pd, Ag, In, Au and Pb", Japan. J. Appl. Phys., vol. 16, No. 5, May 1977, pp. 705-717.

Ando and Uyeda, "Preparation of Ultrafine Particles of Refractory Metal Carbides by a Gas-Evaporation Method", J. Crystal Growth, vol. 52, 12/1981, pp. 178-181.

Kaito "Coalescence Growth of Smoke Particles Prepared by a Gas-Evaporation Technique", Japan. J. Appl. Phys., vol. 17, No. 4, Apr. 1978, pp. 601-609.

Shiojiri et al., "Coalescence Growth of Metal Smoke Particles Prepared by Gas Evaporation", J. Crystal Growth, vol. 52, 12/1981, pp. 168-172.

*Primary Examiner*—L. Dewayne Rutledge
*Assistant Examiner*—S. Kastler
*Attorney, Agent, or Firm*—Edward W. Callan

[57] ABSTRACT

In a system and method for producing ultrafine particles and ultrafine fibers of a given source material by evaporating and condensing the material in a gas atmosphere that includes inert gas. A smaller, more narrow size distribution is accomplished by producing the particles and fibers in a microgravity environment in order to reduce particle coalescence caused by convection currents. Particle coalescence also is reduced in an Earth gravity environment by controlling the convection currents. Condensed particles are collected either by providing an electrostatic field or a spatially varying magnetic field or by causing the gas to move through a filter which collects the particles. Nonferromagnetic material fibers are produced and collected by electrodes which produce an electro- static field. Ferromagnetic particles are collected by spatially varying magnetic fields.

32 Claims, 7 Drawing Sheets

ULTRAFINE PARTICLE AND FIBER PRODUCTION IN MICROGRAVITY

This invention was made with Government support under contract NAS8-35279 awarded by NASA. The Government has certain rights in this invention.

BACKGROUND OF THE INVENTION

The present invention generally pertains to the production of ultrafine particles and fibers and is particularly directed to the production of ultrafine particles and fibers of a given material by evaporating and condensing the material in an atmosphere of inert gas.

Ultrafine particles are defined herein as particles having characteristic dimensions of from 10 angstroms to 1 micron. The present invention is focused on the production of ultrafine particles in the range of from 100 to 1000 angstroms.

Ultrafine fibers are defined herein as fibers having diameters in the same range, from 100 to 1000 angstroms, and lengths at least three times longer than their diameters.

Ultrafine particles and ultrafine fibers have several unique features that make them particularly attractive for many applications. These features include (a) large surface area per unit volume, (b) at least one very small dimension, and (c) many boundaries per unit volume.

For example, 100 angstrom particles have a very large specific surface area of 600 m$^2$/cc. Thus, particles having a dimension as small as 100 angstroms have very rapid response in chemical diffusion reactions (fast kinetics) and to thermal stimuli (fast thermal response times). Also 100 angstrom particles can provide of order of 10$^6$ boundaries (interfaces) per linear cm of length and thus produce matter in a very heterogeneous state.

Techniques for preparing ultrafine particles and ultrafine fibers by an evaporation and condensation process are described in the following publications:

Kimoto et al., "An Electron Microscope Study on Fine Metal Particles Prepared by Evaporation in Argon Gas at Low Pressure", Japan. J. Appl. Phys., Vol. 2, No. 11, Nov. 1963, pp. 702-713.

Tasaki et al, "Magnetic Properties of Ferromagnetic Metal Fine Particles Prepared by Evaporation in Argon Gas", Japan. J. Appl. Phys., Vol. 4, No. 10, Oct. 1965, pp. 707-711.

Kimoto and Nishida, "An Electron Microscope and Electron Diffraction Study of Fine Smoke Particles Prepared by Evaporation in Argon Gas at Low Pressures (II)", Japan. J. Appl. Phys., Vol. 6, No. 9, Sept. 1967, pp. 1047-1059.

Yatsuya et al., "Formation of Ultrafine Metal Particles by Gas Evaporation Technique. I. Aluminum in Helium", Japan. J. Appl. Phys., Vol. 12, No. 11, Nov. 1973, pp. 1675-1684.

Wada and Ichikawa, "A Method of Preparation of Finely Dispersed Ultrafine Particles", Japan. J. Appl. Phys., Vol. 15, No. 5, May 1976, p. 755-756.

Kato, "Preparation of Ultrafine Particles of Refractory Oxides by Gas-Evaporation Method", Japan. J. Appl. Phys., Vol. 15, No. 5, May 1976, pp. 757-760.

Granqvist and Buhrman, "Ultrafine Metal Particles", J. Appl. Phys., Vol. 47, No. 5, May 1976, pp. 2200-2219.

Kaito et al., "Growth of CdS Smoke Particles Prepared by Evaporation in Inert Gases", J. Appl. Phys., Vol. 47, No. 12, Dec. 1976, pp. 5161-5166.

Hayashi et al., "Formation of Ultrafine Metal Particles by Gas-Evaporation Technique. IV. Crystal Habits of Iron and Fcc Metals, Al, Co, Ni, Cu, Pd, Ag, In, Au and Pb", Japan. J. Appl. Phys., Vol. 16, No. 5, May 1977, pp. 705-717.

Kaito "Coalescence Growth of Smoke Particles Prepared by a Gas-Evaporation Technique", Japan. J. Appl. Phys., Vol. 17, No. 4, April 1978, pp. 601-609.

Shiojiri et al., "Coalescence Growth of Metal Smoke Particles Prepared by Gas Evaporation", J. Crystal Growth, Vol. 52, 1981, pp. 168-172.

Ando and Uyeda, "Preparation of Ultrafine Particles of Refractory Metal Carbides by a Gas-Evaporation Method", J. Crystal Growth, Vol. 52, 1981, pp. 178-181.

The technique used in the present invention is that of evaporation of material into an inert gas. Condensation ensues when the evaporated material expands into the inert gas and is cooled by the gas. A reactive gas may be mixed with the inert gas in order to alter the composition of the condensed material. Condensation can be divided into a three step process. First the expanding vapor becomes supersaturated and very small embryos condense in the vapor. Then the embryos grow into larger particles by additional vapor diffusing through the inert gas and condensing onto the embryos. Last, the particles collide and coalesce into larger particles. The coalescence rate depends on the particle density.

Resistively heated evaporation sources are commercially available in several refractory metals, principally tungsten (W), molybdenum (Mo), and tantalum (Ta). Some heaters are also available with either a refractory oxide coating or with a non-metallic crucible.

Condensation includes all of the particle growth processes that take place between the initial stages of condensation from vapor and the final collection of the particles. It is useful to divide the growth processes into three distinct stages: (a) embryo formation (the smallest particles), (b) diffusion of vapor to particles, and (c) particle coalescence. Embryo formation and accretion of vapor by particles are not strictly distinct stages. Particle coalescence is believed to be more distinct from the others.

Collection of particles is the final step. Convection insures that particles are moved rapidly over large distances in the experimental apparatus. Eventually they adhere to surfaces, making their collection easy.

It is useful to set the scale of important physical parameters under typical conditions. Set forth below are the parameters for an example using helium (He) as an inert gas and palladium (Pd) as the evaporated material condensing into 100 angstrom particles. The source temperature is taken to be 2000 K where Pd has a vapor pressure of 1 torr. All quantities refer to 2000 K and a He pressure of 10 torr. The gas is assumed to be an ideal Maxwell gas and the Pd particles are assumed to in the free molecular regime because they have Knudsen numbers, $K_n$, that are greater than 10.

| Inert Gas | Particles | |
|---|---|---|
| P = 10 torr | P (vapor) = | 1 torr |
| T = 2000K | T = | 2000K |
| | d = | particle diameter |
| | = | 100 angstroms |
| $N_g$ = gas density | $N_p$ = | particle density |
| = 5 × 10$^{16}$/cm$^3$ | = | 1 × 10$^{11}$/cm$^3$ |
| $V_g$ = gas mean speed | $V_p$ = | particle mean speed |
| 3 × 10$^5$ cm/s | = | 4 × 10$^2$ cm/s |

| Inert Gas | Particles |
|---|---|
| $L_g$ = gas mean free path | $L_p$ = particle apparent mfp |
| = $1 \times 10^{-2}$ cm | = $1 \times 10^{-2}$ cm |
| $D_g$ = gas diffusion coeff. | $D_p$ = particle diffusion coeff. |
| = $4 \times 10^3$ cm$^2$/s | = 2 cm$^2$/s |
| | $K_n$ = $2 \times L_g/d$ |
| | = $2 \times 10^4$ |

Because of the higher temperatures and lower pressures, these diffusion coefficients and mean free paths are larger than usually encountered.

Embryos form very close to the source because of the large temperature gradients. For the example of Pd evaporation at 2000 K, it is calculated that the vapor need only be cooled by 29 K in order to be supersaturated by 30% (Sp=1.3). This temperature drop takes place within a few tenths of a mm of the source without convection. With convection it is not possible to make as general a statement, however it seems likely that there are still strong temperature gradients near the source.

Once embryos are formed with greater than a critical radius, $R^*$, it is energetically favorable for them to grow. The ensuing growth of embryos and the birth of new ones has been analyzed in a publication by Dunning, "Nucleation, Growth, Ripening and Coagulation in Aerosol Formation", Symposia of the Faraday Society, No. 7, p. 7 (1973).

Following Dunning, imagine that at time zero there is a vapor which is out of equilibrium and free of any nuclei. The first generation of embryos are then born. Here we do not consider nucleation kinetics except to note that when the system is far from equilibrium they are rapid and become slow near equilibrium as Sp≃1.

First-born embryos grow by the diffusion and accretion of vapor and second generation embryos are then born. The radius of the first born embroyos grows as a function of time.

As the existing embryos grow, they deplete the system of vapor and thus $R^*$ increases. With increasing $R^*$, the birth-rate of new embryos (the number born per unit time), diminishes.

Eventually, the birthrate becomes very small. The older generation embryos continue to accrete vapor, however, thereby increasing $R^*$. Younger embryos can then have radii smaller than $R^*$, and must begin to evaporate.

The single particle processes leading up this point produce a distribution of particle sizes even though the particles are assumed to be born with a very narrow range of sizes. However, the distribution decreases monotonically from a maximum size in contradistinction to what is observed. What is observed is a broad distribution with a tail extending to large sizes. This is due to the process of two or more particles coalescing, as discussed below.

It is observed that the particle distribution in many systems has a long tail extending to large sizes. This is true of numerous types of systems including aerosols and fine particles produced by the evaporation and condensation in inert gas technique. Frequently, the observed distributions are found not to be Gaussian in particle size but to be better represented by a lognormal distribution which is Gaussian in the logarithm of the particle size, as in publications by Fuchs and Sutugin, "Aerosol Science", Academic Press, p. 1 (1966), and Granqvist and Buhrman, J. Appl. Phys. Vol. 47, p. 2200 (1976).

Granqvist and Buhrman describe a lognormal distribution of fine particles of aluminum (Al) condensed in an argon (Ar) and oxygen ($O_2$) atmosphere. The addition of $O_2$ is thought to lead to smaller particles. $O_2$ does, however, produce an oxide layer on the particles. The presence of the oxide layer does not appear to affect the lognormal distribution.

There is also a large spatial inhomogeneity in particle size due to convection.

Yatsuya et al., "Formation of Ultrafine Metal Particles by Gas Evaporation Technque. I. Aluminum in Helium", Japanese J. Appl. Phys. Vol 12, p. 1675 (1973) describe the variation of particle size distribution within a work chamber for evaporating and condensing ultrafinefine particles in an inert gas. Such variation is dominated by convective processes. Visually a convecting plume of particles is quite inhomogeneous, containing one or more dark bands and exhibiting changes with time.

The major point to be inferred from Yatsuya et al. is that there is a spatial variation of matter density within a plume. It is believed that this variation exists in part because the particle number density is strongly varying within the plume.

Smoluchowski (Phys. Z., Vol. 17, pp. 557 et. seq., 585 et. seq. (1916); Z. Phys. Chem., Vol. 92, p. 129 (1918)) was among the first to examine the coalescence or coagulation rate in a system of particles. He found that for a system of N identical particles per unit volume the time rate of change of particle density is $$dN/dt = -K_o N^2 \qquad (1)$$

$K_o$ is a coagulation coefficient so that N decreases with time. It is significant that the rate of decrease is proportional to N squared.

Hidy and Brock teach that when there is a distribution of particle sizes then the net rate of change of the number of particles of size $N_k$ is equal to the sum of a creation term and a destruction term.

$$dN_k/dt = \tfrac{1}{2} \sum_{i+j=k} K_{ij} N_i N_j - N_k \sum_i K_{ik} N_i \qquad (2)$$

Care must be taken in equation 2 not to count events twice etc. The destruction term above causes the exhaustion of the smallest particles in order to produce larger ones. In addition, note that the time rate of change of particle number within a distribution varies as N squared.

Even if the initial particle distribution were monodisperse, the collisions within a plume, described by Yatsuya et al. leads to a dispersion in particle size by coalescence.

Any process which produces a relative velocity between particles contributes to coalescence due to particle-particle collisions. Some important processes are: (a) thermal diffusion (b) laminar and turbulent flow fields (c) electric and magnetic forces (d) gravitational and centrifugal force fields, and (e) others.

Thermal diffusion of particles is important because it is always present. It leads to a binary collision rate density, $L_{ij}$ between particles of Mass $M_i$ and $M_j$ given by $$L_{ij} = C_{ij} \sqrt{(8 \pi KT(1/M_i + 1/M_j))} R_{ij}^2 N_i N_j \qquad (3)$$

Hidy and Brock, "The Dynamics of Aerocolloidal Systems", Pergamon Press (1970).

$C_{ij}$ is either $\frac{1}{2}$ or 1, K is Boltzmann's constant and $R_{ij}$ is the collision radius of interaction. $L_{ij}$ can be related to the coalescence rate by making assumptions about sticking coefficients. From equation 3, it is noted that (i) larger particles are relatively more important because of $R_{ij}$, and that (ii) the rate is proportional to $N_iN_j$.

Laminar and turbulent flow fields cause particles to collide because of shear in the velocity fields. Electric and magnetic forces give a relative velocity between particles if the particles have opposite charges, induced dipole moments or intrinsic magnetic moments, as examples among many possibilities. Gravitational and centrifugal force fields cause collisions because heavier particles settle out faster.

The effects of coalescence within a convecting plume are more severe than the above remarks would indicate. FIG. 1 shows a qualitative sketch of the flow lines within a convecting plume.

Initially, evaporated material leaves the source 10 in a 4 pi solid angle, as sketched in FIG. 1. It is assumed that evaporated material condenses into particles within a few mm of the source, more rapidly at the bottom and more slowly at the top due to convection. The convecting inert gas flow rises from below, however, and "folds" up the evaporated and condensed material into a rising plume of particles and heated inert gas, much like a candle flame. In addition, some particles pass by the source several times because of large scale convection in the work chamber.

Thus there are serious consequences for the coalescence rate due to gravity driven convection. Concentrating the particles from an expanding 4 pi solid angle spatial distribution into a narrow rising plume causes the number of particles per unit volume in the plume to be increased. The particle collision rate is thus greatly increased, as can be seen from equation (1).

SUMMARY OF THE INVENTION

The present invention provides a smaller more narrow distribution of ultrafine particles produced by evaporation and condensation in an inert gas atmosphere by producing the particles in a microgravity environment. The microgravity environment may be provided in an orbitting Earth satellite or space station, a drop tower or an aircraft in a microgravity trajectory.

In the absence of gravity, evaporated material leaves the source in a 4 pi solid angle. Vapor cools in the imposed temperature gradient and particles condense within a few mm of the source also. The particles diffuse outward in the presence of the temperature gradient (thermophoresis) and applied external forces. As the particles move further from the source, the number density decreases for geometric reasons, and the rate of coalescence decreases as the particles move outward.

The particle density is decreased by an order of magnitude over what it is with convection. Assuming other parameters being constant, there is a two order of magnitude decrease in the coalescence rate of small particles into large ones.

Once convection has been suppressed, the movement of particles is greatly slowed, whereby the work chamber could become clogged with particles in the absence of some means for collecting the particles in the microgravity environment.

Accordingly, the system of the present invention further includes means for collecting the condensed particles. The collection methods used include the application of an electrostatic field for attracting material, the application of a magnetic field for attracting ferromagnetic material, and causing the inert gas to flow through a filter. These collection methods also are applicable in a normal Earth gravity as separate aspects of the present invention.

An unexpected result of the application of an electrostatic field to attract nonferromagnetic material was the formation of ultrafine fibers from the condensed particles. This aspect of the present invention also is applicable in a normal Earth gravity environment for the production of ultrafine fibers.

Additional features of the present invention are described in relation to the description of the preferred embodiments.

DESCRIPTION OF THE PREFERRED EMBODIMENTS

Figure 2:
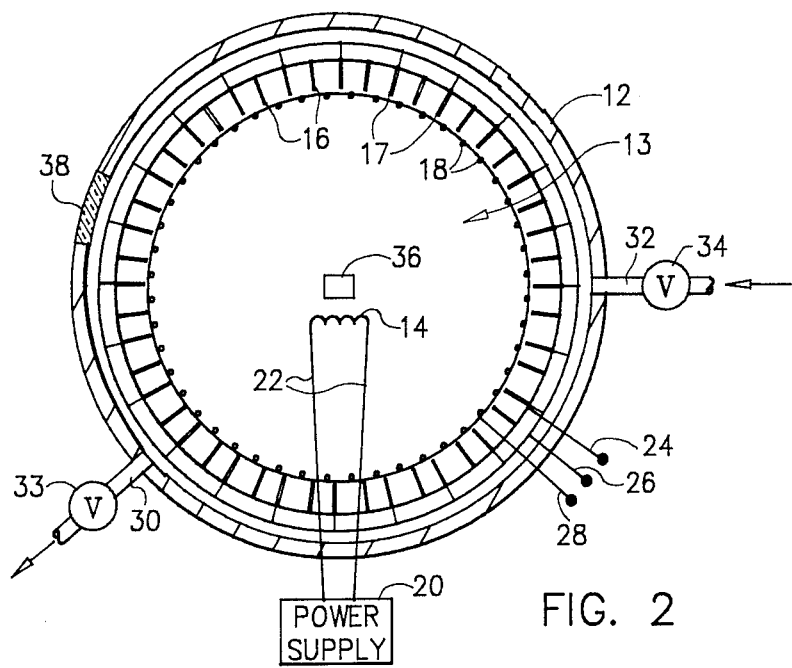
FIG. 2 is a schematic drawing of a preferred embodiment of the particle production system of the present invention for use in a microgravity environment and including electrostatic collection means.

Referring to FIG. 2, one preferred embodiment of the particle and fiber production system of the present invention for use in a microgravity environment includes a spherical container 12 (shown schematically in section) defining a work chamber 13 and containing a source material evaporator 14 and a plurality of electrodes 16, 17, 18 positioned along the inside surface of the container 12.

The evaporator 14 is a resistance heater that is powered by a power souce 20 connected thereto by lines 22. Other methods of heating also may be used.

The electrodes include a plurality of pairs of opposing conductive plates 16, 17 that are charged to different potentials and a plurality of wires 18 that are charged to a potential intermediate to the respective potentials of the plates 16, 17. Each wire 18 is positioned adjacent a pair of the plates 16, 17 in a plane that is parallel to and between the pair of plates 16, 17. The wires 18 are positioned in a portion of the container 12 in which the particles condense.

All of the plates 16 that are charged to one potential are connected in common to a wire 24, and all of the plates 17 that are charged to a different potential are connected in common to a wire 26. All of the wires 18 are connected in common to a wire 28. The wires 24, 26, and 28 are respectively connected to power supplies (not shown) having different bias voltages. The electrodes 16, 17, 18 provide a spatially varying electrostatic field in the work chamber 13 for attracting particles to the electrodes.

Although only one circular array of electrodes 16, 17, 18 is shown in the FIG. 2, it is to be understood that there are multiple arrays of electrodes within the container 12.

The container 12 is connected to a gas line 30 that is connected to a vacuum pump (not shown) and is further connected to a gas line 32 that is connected to a source of an inert gas (not shown). The gas line 30 includes a cut-off valve 33; and the gas line 32 includes a cut-off valve 34.

A charge 36 of the given material to be evaporated is placed in the evaporator 14. The work chamber 13 is evacuated of air by the vacuum pump through the gas line 30 and the valve 33 is closed. The valve 34 is then opened and an inert gas is provided into the work chamber 13 through the gas line 32. The valve 32 is then closed.

The charge 36 of the source material is then evaporated by the evaporator 14 and the vaporized material disperses radially in a solid 4 pi angle from the charge 36. The vaporized particles of the source material then condense and are collected by the electrodes 16, 17, 18.

The container 12 also includes a window 38 for enabling observation of the particle production and collection process.

Figure 3:
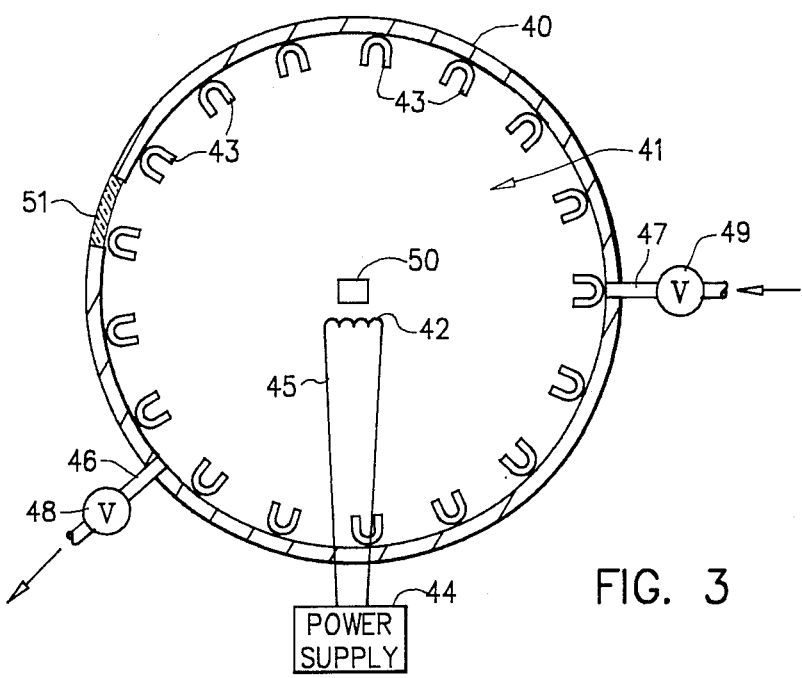
FIG. 3 is a schematic drawing of a preferred embodiment of the particle production system of the present invention for use in a microgravity environment and including magnetic collection means.

Referring to FIG. 3, another preferred embodiment of the particle production system of the present invention for use in a microgravity environment includes a spherical container 40 (shown schematically in section) defining a work chamber 41 and containing a source material evaporator 42 and a plurality of magnets 43 positioned along the inside surface of the container 40.

As in the embodiment of FIG. 2, the evaporator 42 is a resistance heater that is powered by a power source 44 connected thereto by lines 45.

The magnets 43 provide a spatially varying magnetic field in the work chamber 41 for attracting particles to the magnets 43.

Although only one circular array of magnets 43, is shown in the FIG. 3, it is to be understood that there are multiple arrays of magnets within the container 40.

The container 40 is connected to a gas line 46 that is connected to a vacuum pump (not shown) and is further connected to a gas line 47 that is connected to a source of an inert gas (not shown). The gas line 46 includes a cut-off valve 48; and the gas line 47 includes a cut-off valve 49.

A charge 50 of the given material to be evaporated is placed in the evaporator 42. The work chamber 41 is evacuated of air by the vacuum pump through the gas line 46 and the valve 48 is closed. The valve 49 is then opened and an inert gas is provided into the work chamber 41 through the gas line 47. The valve 32 is then closed.

The charge 50 of the source material is then evaporated by the evaporator 42 and the vaporized material disperses radially in a solid 4 pi angle from the charge 50. The vaporized particles of the source material then condense and are collected by the magnets 43.

The container 40 also includes a window 51 for enabling observation of the particle production and collection process.

Figure 4:
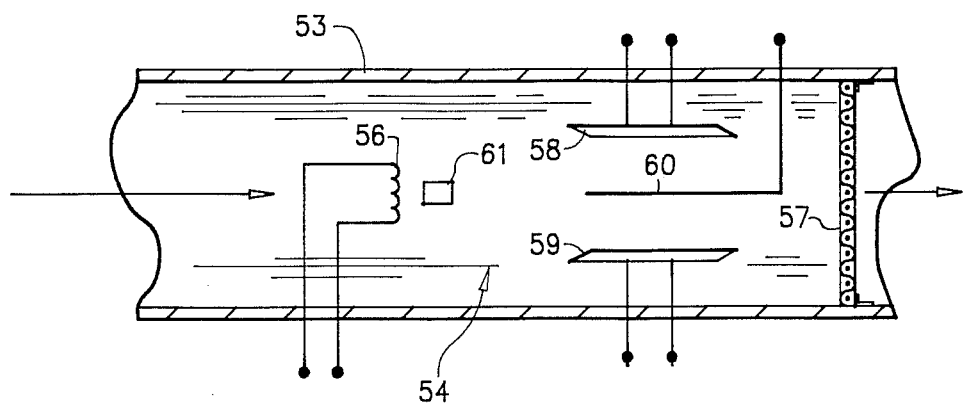
FIG. 4 is a schmematic drawing of a preferred embodiment of the particle production system of the present invention for use in a microgravity environment and including a filter for collecting the particles.

Referring to FIG. 4, another preferred embodiment of the particle production system of the present invention for use in a microgravity environment includes a cylindrical container 53 defining a work chamber 54 and containing a source material evaporator 56, a filter 57, pair of conductive plates 58, 59 charged to different potentials, and a conductive wire 60 charged to a potential intermediate to the potentials of the plates 58, 59.

As in the embodiment of FIG. 2, the evaporator 56 is a resistance heater that is powered by a power source (not shown). The plates 58, 59 and the wire 60 are respectively connected to different bias voltage sources (not shown).

The plates 58, 59 and the wire 60 are charged to provide a spatially varing electrostatic field for attracting particles thereto.

A charge 61 of the given material to be evaporated is placed in the evaporator 56. The work chamber 54 is evacuated of air and inert gas is caused to flow through the work chamber 54 and the filter 57.

The charge 61 of the source material is then evaporated by the evaporator 56 and the vaporized material disperses radially in a solid 4 pi angle from the charge 61. The vaporized particles of the source material then condense and are carried by the flow of the inert gas to the plates 58, 59, the wire 60 and the filter 57 which collect the particles. Ultrafine particles and fibers collect on the wire 60 and the plates 58, 59; and ultrafine particles collect on the filter 57.

In an alternative preferred embodiment (not shown) a magnet is substituted for the plates 58, 59 and the wire 60 in the system shown in FIG. 4 in order to enhance the collection of ferromagnetic material particles.

Figure 5:
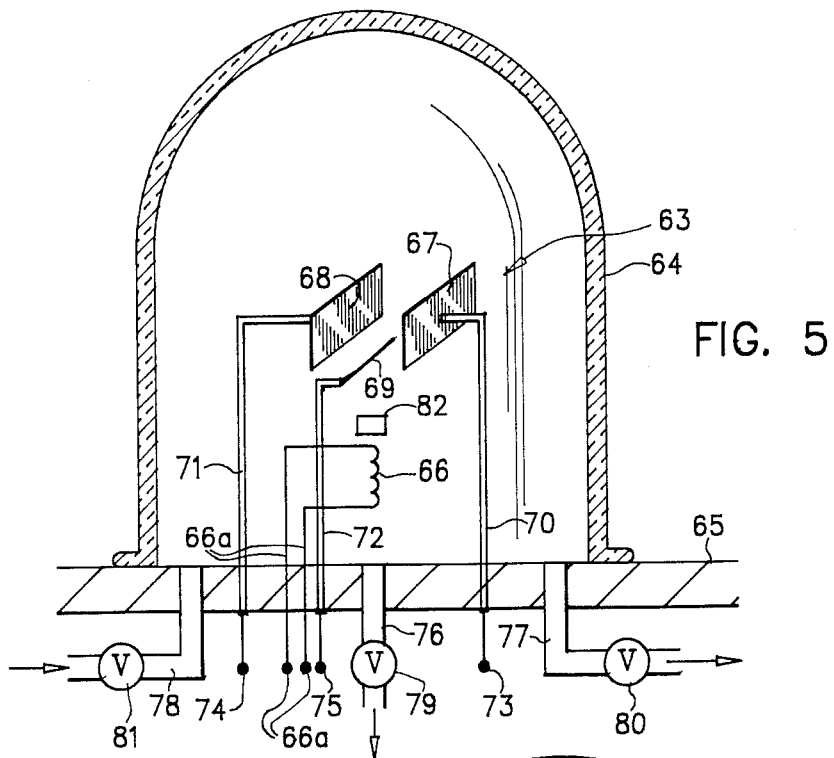
FIG. 5 is a schematic drawing of a preferred embodiment of the particle production system of the present invention for use in and Earth gravity environment and including electrostatic collection means.

Referring to FIG. 5, a preferred embodiment of the particle production system of the present invention for use in an Earth gravity environment includes a sealed work chamber 63 defined by a dome 64 and a plate 65 and containing a source material evaporator 66, a pair of conductive plates 67, 68 charged to different potentials and a conductive wire 69 charged to a potential intermediate to the potential of the plates 67, 68.

The evaporator 66 is a resistance heater that is powered by a power source (not shown) connected thereto by lines 66a.

The wire 69 is positioned adjacent the pair of the plates 67, 68, in a plane that is parallel to and between the pair of plates 67, 68. The wire 69 is positioned in a portion of the work chamber 63 in which the particles condense.

The plates 67, 68 and the wire 69 are supported by conductive rods 70, 71, 72, which are respectively connected by wires 73, 74, 75 to power supplies (not shown) having different bias voltages. The plates 67, 68 and the wire 69 provide an electrostatic field in the work chamber 63 for attracting particles thereto.

The chamber 63 is connected to two gas lines 76, 77 that are connected to a vacuum pump (not shown) and is further connected to a gas line 78 that is connected to a source of an inert gas (not shown). The gas line 76 includes a cut-off valve 79, the gas line 77 includes a cut-off valve 80, and the gas line 78 includes a cut-off valve 81.

A charge 82 of the given material to be evaporated is placed in the evaporator 66. The work chamber 63 is evacuated of air by the vacuum pump through the gas line 76 and the valve 79 is closed. The valve 81 is then opened and an inert gas is provided into the work chamber 63 through the gas line 78. The valve 81 is then closed.

Figure 1:
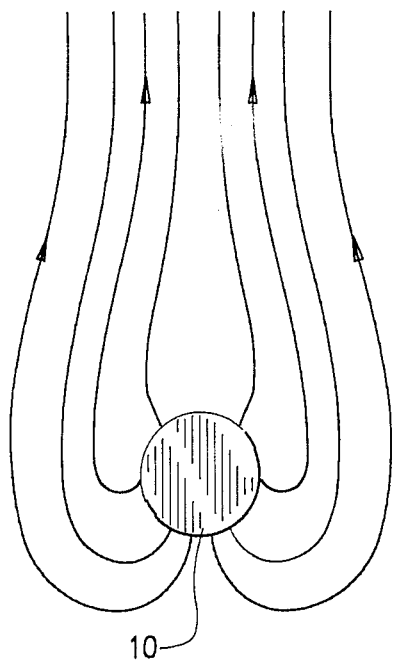
FIG. 1 illustrates the convection flow lines in a plume of evaporated material in a prior art evaporation and condensation system in an Earth gravity environment.

The charge 82 of the source material is then evaporated by the evaporator 66 and the vaporized material initially disperses radially in a solid 4 pi angle from the charge 82, but then is carried into a plume by the convection currents, as shown in FIG. 1. The vaporized particles of the source material then condense and are collected by the plates 67, 68 and the wire 69.

After the particles are collected, the inert gas is evacuated from the work chamber 63 through the gas line 77, and atmospheric air pressure is restored to the work chamber 63 through the gas line 76.

Figure 6:
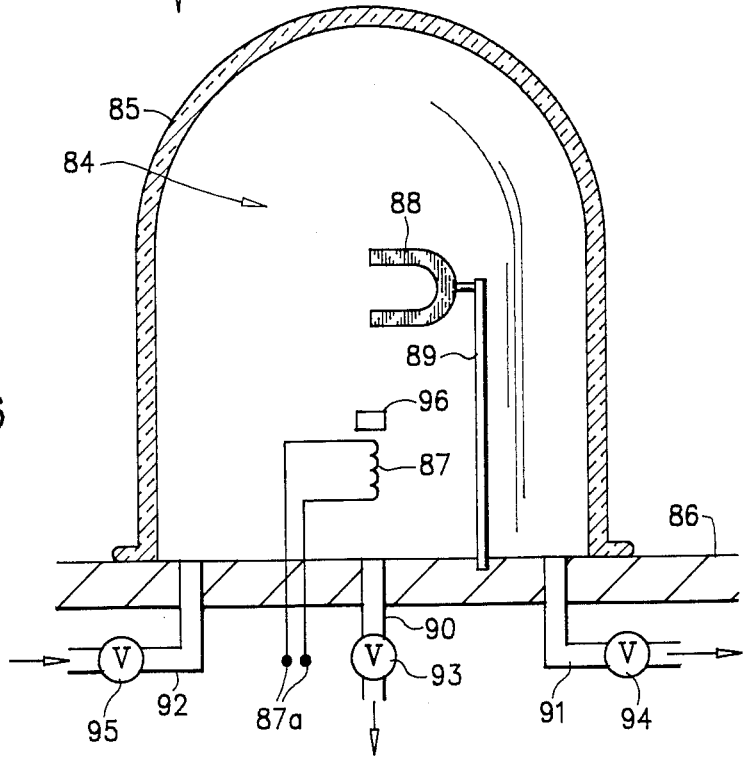
FIG. 6 is a schematic drawing of a preferred embodiment of the particle production system of the present invention for use in an Earth gravity environment and including magnetic collection means.

Referring to FIG. 6, another preferred embodiment of the particle production system of the present invention for use in an Earth gravity environment includes a sealed work chamber 84 defined by a dome 85 and a plate 86 and containing a source material evaporator 87 and a magnet 88.

The evaporator 87 is a resistance heater that is powered by a power source (not shown) connected thereto by lines 87a.

The magnet 88 is positioned in a portion of the work chamber 84 in which the particles condense.

The magnet 88 is supported by a rod 89. The magnet 88 provides a spatially varying magnetic field in the work chamber 84 for attracting particles to the magnet 88.

The chamber 84 is connected to two gas lines 90, 91 that are connected to a vacuum pump (not shown) and is further connected to a gas line 92 that is connected to a source of an inert gas (not shown). The gas line 90 includes a cut-off valve 93, the gas line 91 includes a cut-off valve 94, and the gas line 92 includes a cut-off valve 95.

A charge 96 of the given material to be evaporated is placed in the evaporator 87. The work chamber 84 is evacuated of air by the vacuum pump through the gas line 90 and the valve 93 is closed. The valve 95 is then opened and an inert gas is provided into the work chamber 84 through the gas line 92. The valve 95 is then closed.

The charge 96 of the source material is then evaporated by the evaporator 87 and the vaporized material initially disperses radially in a solid 4 pi angle from the charge 96, but then is carried into a plume by the convection currents, as shown in FIG. 1. The vaporized particles of the source material then condense and are collected by the magnet 88.

After the particles are collected, the inert gas is evacuated from the work chamber 84 through the gas line 91, and atmospheric air pressure is restored to the work chamber 84 through the gas line 90.

Figure 7:
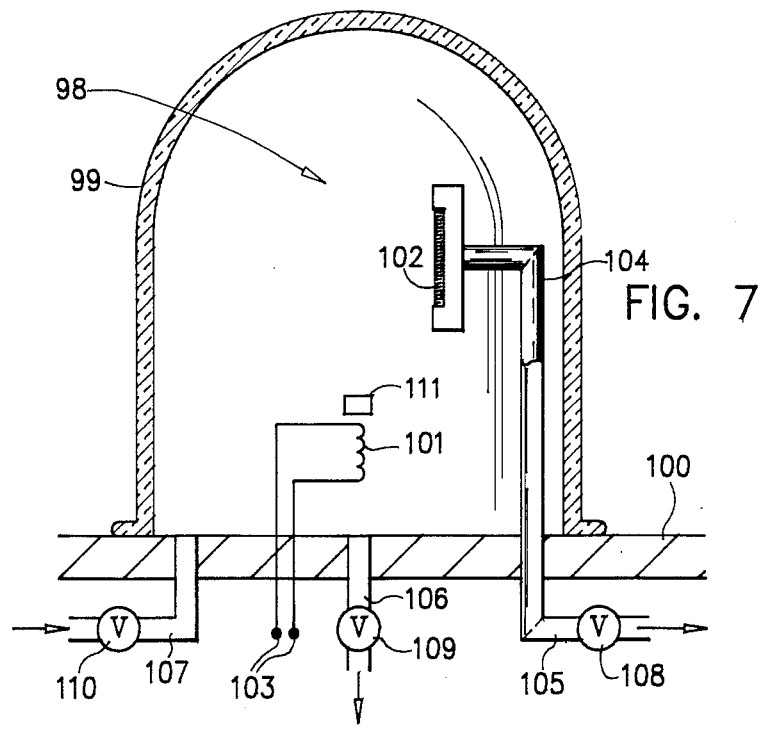
FIG. 7 is a schematic drawing of a preferred embodiment of the particle production system of the present invention for use in an Earth gravity environment and including a filter for collecting the particles.

Referring to FIG. 7, another preferred embodiment of the particle production system of the present invention for use in an Earth gravity environment includes a sealed work chamber 98 defined by a dome 99 and a plate 100 and containing a source material evaporator 101 and a filter 102.

The evaporator 101 is a resistance heater that is powered by a power source (not shown) connected thereto by lines 103.

The filter 102 is positioned in a portion of the work chamber 98 in which the particles condense.

The filter 102 is supported by a pipe 104 that is connected through an opening in the frame 100 to a gas line 105 so that gas flowing through the filter 102 will flow through the gas line 105.

The chamber 98 also is connected to a gas line 106. The gas lines 105 and 106 are connected to a vacuum pump (not shown). The chamber 98 is further connected to a gas line 107 that is connected to a source of an inert gas (not shown). The gas line 105 includes a cut-off valve 108, the gas line 106 includes a cut-off valve 109, and the gas line 107 includes a cut-off valve 110.

A charge 111 of the given material to be evaporated is placed in the evaporator 101. The work chamber 98 is evacuated of air by the vacuum pump through the gas line 106 and the valve 109 is closed. The valves 108 and 110 are then adjusted to cause inert gas to flow into the chamber 98 through the gas line 107 and out of the chamber 98 through the gas line 105 while maintaining the desired pressure within the work chamber 98.

The charge 111 of the source material is then evaporated by the evaporator 101 and the vaporized material initially disperses radially in a solid 4 pi angle from the charge 111, but then is carried into a plume by the convection currents, as shown in FIG. 1. The vaporized particles of the source material then condense and are carried by the flow of inert gas to the filter 102 where they are collected.

Figure 8:
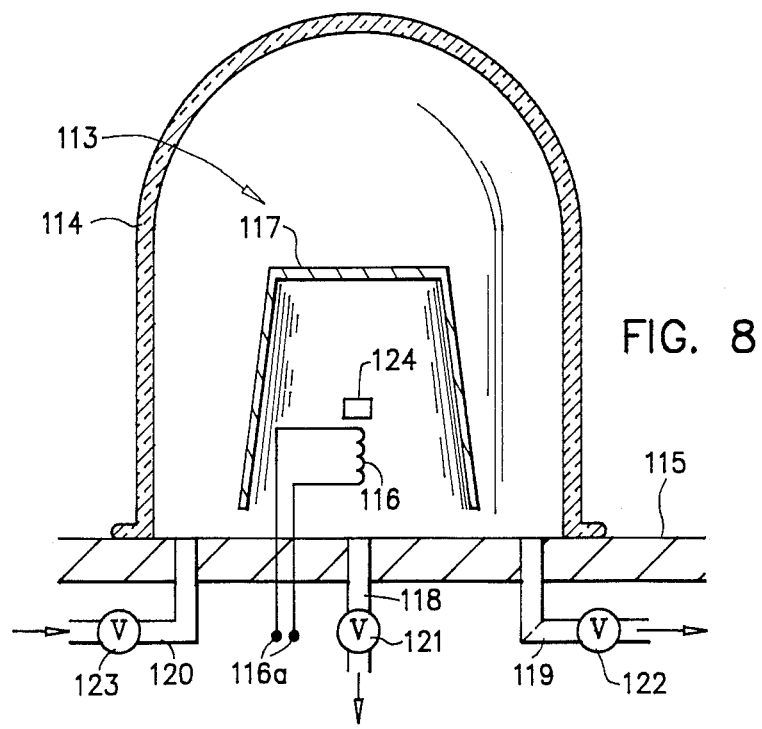
FIG. 8 is a schematic drawing of a preferred embodiment of the particle production system of the present invention for use in an Earth gravity environment and including means for controlling the convection currents to reduce particle coalescence.

An embodiment of the particle production system of the present invention for use in an Earth gravity environment, wherein the convection currents are controlled to reduce coalescence to less than what the coalescence would be but for such control is described with reference to FIG. 8. This embodiment includes a sealed work chamber 113 defined by a dome 114 and a plate 115 and containing a source material evaporator 116 and a hat 117.

The evaporator 116 is a resistance heater that is powered by a power source (not shown) connected thereto by lines 116a.

The hat 117 is positioned in a portion of the work chamber 113 in which the particles condense.

The hat 117 alters the flow of the convection currents so as to reduce coalescence due to gravity to less than the coalescence would be in the absence of the hat 117.

The chamber 113 is connected to two gas lines 118, 119 that are connected to a vacuum pump (not shown). The chamber 113 is further connected to a gas line 120 that is connected to a source of an inert gas (not shown). The gas line 118 includes a cut-off valve 121, the gas line 119 includes a cut-off valve 122, and the gas line 120 includes a cut-off valve 123.

A charge 124 of the given material to be evaporated is placed in the evaporator 116. The work chamber 113 is evacuated of air by the vacuum pump through the gas line 118 and the valve 121 is closed. The valve 123 is then opened and inert gas flows into the work chamber 113 through the gas line 120.

The charge 124 of the source material is then evaporated by the evaporator 116 and the vaporized material initially disperses radially in a solid 4 pi angle from the charge 124, but then is carried into convection currents within the hat 117. The vaporized particles of the source material then condense and are collected on the hat 117 and the floor of the chamber 113.

In an alternative preferred embodiment (not shown), convection currents within a work chamber are controlled to reduce coalescense of the particles by constructing the work chamber along the principles of a diffusion cloud chamber as described by Langsdorf, "A Continuously Sensitive Diffusion Cloud Chamber", Rev. Sci. Inst., Vol. 10, p. 91 (1939).

Ultrafine particles and ultrafine fibers were produced using the production systems of FIGS. 5 and 6. The system of FIG. 5 was used with nonferromagnetic materials and the system of FIG. 6 was used with ferromagnetic materials.

The inert gas pressure in the work chamber is in the range of 0.1 torr to 1 atm. The source material vapor pressure is in the range of 0.1 torr to 10 torr.

For many materials of interest, temperatures of 1500 to 2500 K are required to achieve vapor pressures in the range 0.1 to 10 torr. For this reason, the heating techniques appropriate to this range must meet the following criteria: (a) temperature capability of 1500 to 2500 K, (b) minimum contamination of charge, (c) minimum degradation of heater components, (d) compatibility with zero gravity, (e) compatibility with or providing sample positioning, and (f) energy efficiency.

The systems of FIGS. 5 and 6 were built around a modified Edwards Model E600 vacuum coater.

Ultrafine particle and ultrafine fiber samples were produced in an inert gas atmosphere of either helium or argon, both of stated purity 99.998. At 100 torr inert gas pressure, the stated impurity content corresponds to an impurity level of $2 \times 10^{-3}$ torr.

Resistively heated evaporation sources are commercially available in several refractory metals, principally tungsten (W), molybdenum (Mo), and tantalum (Ta). Some heaters are also available with either a refractory oxide coating or with a non-metallic crucible.

Heaters in W, Mo, or Ta in the form of single filament or triple filament are preferred.

The source material charge to be evaporated was usually in the form of wire, foil or pellets. The pellets were simply placed in a conical basket heater in contact with the filament. Wire and foil charges were wrapped tightly around the filaments. In the latter case the charge melting points gave a calibration point for heater temperature with other temperatures being estimated in the early stages of the work. Later a thermocouple (type K) in contact with the heater was used for measurements at lower temperatures.

W filament heaters worked well at providing high temperatures with modest currents (60 amps.). They did require care, because once heated to high temperatures they display low temperature brittleness (near room temperature). They were used as sources for the following elements:

Al, Ag, Pd, Mg, Fe, Ni, In, Cu

No heater failures were observed, but it was clear that a pronounced reaction was taking place between the heaters and Pd and Ni.

A potentially useful effect was noted. Capillary forces seem to be unusually strong between multifilament W heaters and molten Al. When an Al charge in the form of foil compact was wrapped around the outer portions of a triple 30 mil filament and then melted it would wick into the center portion of the heater with extreme rapidity. This effect is useful for the continuous feeding of Al to the heater; and could be exploited if the space shuttle external tank is eventually taken into orbit. Melted, it would wick into the center portion of the heater with extreme rapidity. It seems evident that this effect is potentially useful for the continuous feeding of Al charge to a heater. In that case 57,000 lb of Al alloy will be available for reprocessing into new forms. Evaporation of thin Al films for mirrors and concentrators and thicker foils for structural members will become attractive. Purification of the Al by vacuum distillation or the preparation of Al alloys by co-deposition of material from two or more sources will become a possibility. For such applications W multifilament heaters or porous sintered compact W heaters could be fed a new Al charge continuously, possible simplifying the hardware and improving the quality of the deposit.

Induction heating also offers many desirable features. These include no contact with the specimen and positive sample positioning by electromagnetic forces. It appears that in one g (gravity), the coil must be rather tightly coupled to the sample in order to levitate it. The proximity of the coil to the specimen tends to block vapor, however, which is not desirable.

In microgravity, however, only weak positioning forces are needed. It is noteworthy that a NASA 1200 W rf induction power supply has been developed and is qualified for operation in the materials science lab located in the orbiter payload bay. It is described in a NASA document entitled "Microgravity Science and Applications".

For the system of FIG. 5, electrodes consisting of 7×9 cm rectangular copper plates 67,68 were introduced into the workchamber 63. They were positioned from 5 to 10 cm above the charge of the source material 82 so that the plume rose between them. Plate separations from 2 to 4 cm were used. One plate was grounded and the other connected to a 0 to −5 kV dc supply. The charged plate had rounded edges and was polished.

In a vacuum, 5kV can be applied without breakdown. When He gas was introduced, breakdown occurred from 170 to 600 V depending on pressure. Inert gas pressures from 1 to 600 torr were used.

For some sample runs, the corona discharge wire 69, of 5 to 20 mil diameter was placed in the plume. Most samples were produced with a 7 mil wire parallel to the plates near the bottom edge, as shown in FIG. 5. The wire was connected to a 0 to −3 kv dc supply. No breakdown or corona was observed when the work chamber 63 was in vacuum. When He was introduced, a corona around the wire was initiated at 100 to 600 V dc.

Different elements were evaporated from resistance heaters below the source in typically 100 torr of He. The materials were: Al, Zn, Pd, Ag, and Cu. Most experiments were done with Al.

The heater was energized with a 60 amp low voltage ac current and an incandescent plume formed. The plume passed across the corona wire 69 and between the plates 67,68. Without voltages applied to the wire or plates, the plume rose vertically. Large convection patterns, on the order of 10 to 30 cm, were evident in the work chamber 63. A fine, in most cases grey, deposit formed over most of the system. With no voltage applied to the plates 67, 68 or to the wire 69, no fibers were observed to form in excess of the minimum observable length of about one mm.

When the corona wire 69 and the plates 67,68 were charged, typically to - 400 Vdc, the plume was deflected by one cm or more when it rose between the plates. Turning on and off either voltage supply clearly caused the plume to move. Electrostatic plume deflection was observed with all the above elements.

Figure 9:
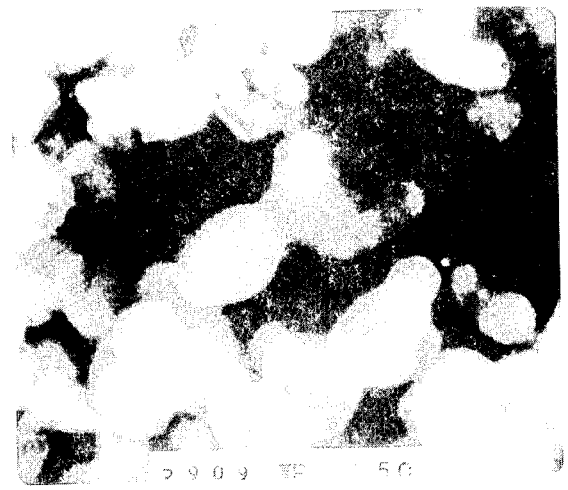
FIG. 9 is a transmission electron micrograph (TEM) at 250,00 times magnification of Pd particles produced in accordance with the present invention in an Earth gravity environment in the absence of an applied electrostatic field.

With either the corona wire 69, or the plates 67,68 charged, fibers or whiskers began to form a few seconds into a run. They were strongly blown about in the convecting gas. FIG. 9 shows an example of Pd particles produced using the system of FIG. 5 without an electrostatic field being applied. Note the clear signs of collisions and inter-particle sintering.

Figure 10:
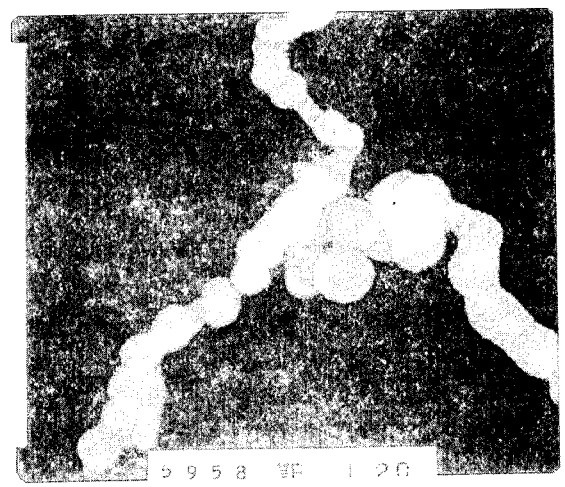
FIG. 10 is a TEM at 120,000 times magnification of Pd particles produced in accordance with the present invention in an Earth gravity environment in the presence of an applied electrostatic field.

FIG. 10 shows an example of ultrafine Pd fibers produced using the system of FIG. 5 with an electrostatic field being applied. The fibers grew preferentially on the charged electrodes 67, 68, 69 to lengths on the order of two cm in times less than a minute. In a few runs using Al, fibers up to 10 cm were grown.

After the heater (evaporator 66) was turned off, convection continued for several minutes as the heater cooled. During this time floating fibers were observed to experience torques and forces as they passed the charged electrodes 67, 68, 69. Eventually the fibers adhered to the charged electrodes, particularly to regions of high field gradient. The gas was cleaned of floating fibers in this way, as expected.

The extent to which convection enhanced or hindered fiber growth was not determined.

However, during a production run, convection produces undesired effects on the fibers such as causing them to collect into tangled bundles. Many runs had to be terminated prematurely because the metallic fibers shorted the corona wire 69 and/or the plates 67, 68 to ground. This latter problem was alleviated partially by putting some insulating shields around feedthroughs.

Figure 11:
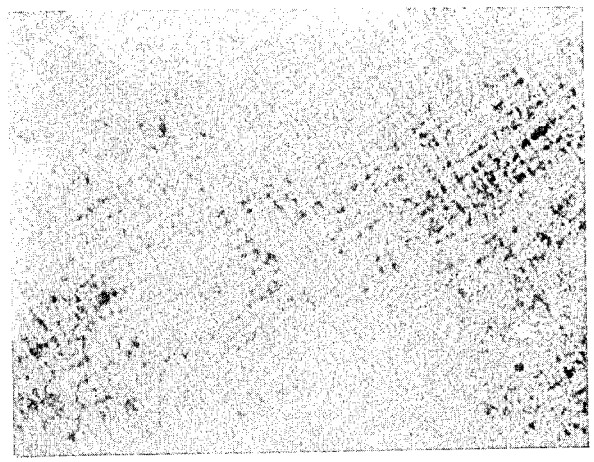
FIG. 11 is an optical photomicrograph at 20 times magnification of Al fiber bundles produced in accordance with the present invention in an Earth gravity environment in the presence of an applied electrostatic field.

After a run, the system was very slowly brought up to atmospheric pressure. Nevertheless, the entering gas blew the fibers into larger bundles. When the system was opened, the He was replaced by air causing the fibers to agglomerate further. FIG. 11 shows a photomicrograph of bundles of Al fibers stuck to one of the plates 67, 68 when it was removed from the system. To prevent the formation of such bundles, the fibers are loaded into protective capsules while still in the work chamber 63.

In an alternative embodiment, the particles were charged by photoejecting electrons. A 10 W germicidal UV lamp with a mercury (Hg) line at 2537 angstroms or 4.97 ev was used to charge the particles. Two experiments (with null results) were carried out on Ag and later Mg. Their work functions are about 4.5 and 3.7 volts, respectively.

In the photoelectric experiments the plume was passed through an electric field of 100 V/cm between the plates, and the UV source was turned on. No plume deflection was noted under any of the conditions investigated.

Turning on the UV did initiate breakdown of the plates 67, 68 when they were operated at higher voltages, however, causing the field to be lowered to that given. In the case of Ag, long fibers grew in a few seconds causing intermittent shorts which burned away. However, in no case was a plume deflection noted.

A ferromagnetic material experiences a strong force in a spatially varying magnetic field. Weakly magnetic materials do also, but the effects are weaker.

For this reason, the system of FIG. 6 was used to produce particles of Fe and Ni. The permanent magnet 88 provided magnetic gradients in the work chamber 84. For both metals material was collected on the magnet 88 and aligned along the field direction as expected.

Unexpectedly, however, large amounts of material condensed elsewhere in the form of 10 cm long fibers which were seen through out the work chamber 84. The fibers, which were later found to form without the presence of the permanent magnets 88, were strongly buffeted by convection.

Figure 12:
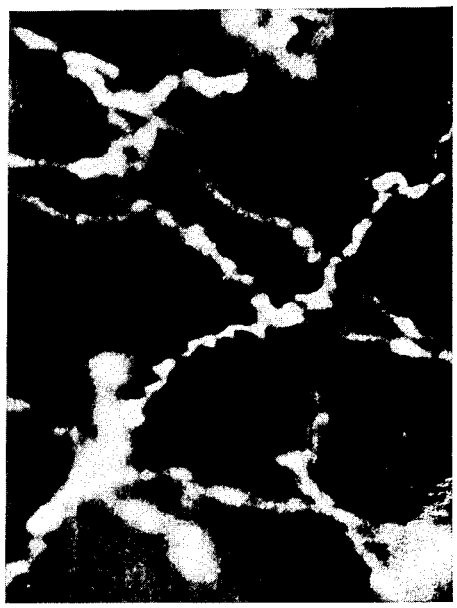
FIG. 12 is a scanning electron micrograph (SEM) at 50 times magnification of Fe fibers collected in accordance with the present invention in an Earth gravity environment.

When the heater was turned off, the fibers slowly settled in the form of copious curtains composed of tangled fiber bundles as shown in FIG. 12.

In Kimoto, Japan. J. Appl. Phys. (1963) cited above, there is reference to "beaded necklaces" of ferromagnetic materials formed during evaporation in an inert gas. It is likely that what is seen in FIG. 12 is the same thing but perhaps grown at a higher evaporation rate.

Opening the work chamber 84 produced strong drafts with the same effects as for the electrostatically produced fibers. Clumps of material floated around the room. Weighing a several cc clump showed it to have density at least 1000 times smaller than that of bulk material.

Scanning electron micrographs showed the material to be composed of many thousands of tangled approximately 500 angstrom fibers. FIG. 12 shows a collection of Fe fibers at 50 times magnification. The bright stripe is the densest part of the bundle where there may be charging.

Figure 13:
FIG. 13 is a scanning electron micrograph (SEM) at 5,000 times magnification of Fe fibers collected in accordance with the present invention in an Earth gravity environment.
Figure 14:
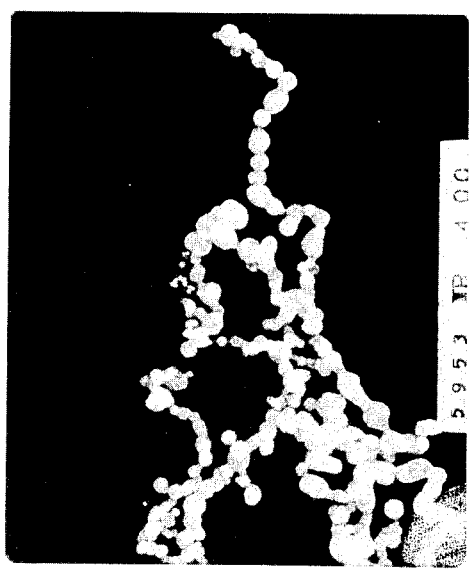
FIG. 14 is a scanning electron micrograph (SEM) at 20,000 times magnification of Fe fibers collected in accordance with the present invention in an Earth gravity environment.

FIGS. 13 and 14 show scanning electron micrographs of the produced Fe fibers at 5,000 and 20,000 times magnification respectively. The fibers are seen to have many kinks but a rather narrow distribution of apparent diameters.

Figure 15:
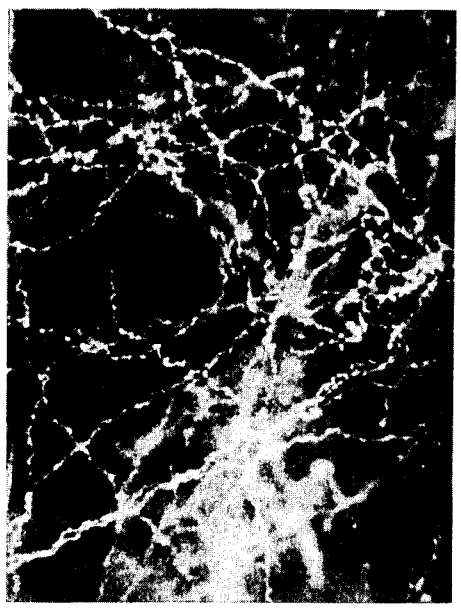
FIG. 15 is a transmission electron micrograph (TEM) at 40,000 times magnification of Fe fibers collected in accordance with the present invention in an Earth gravity environment.

Transmission electron micrographs of the produced Fe fibers reveal more clearly that the fibers were composed of grains, as can be seen in FIG. 15. Also apparent in FIG. 15 is a somewhat larger actual distribution of "diameters" than is evident in FIGS. 14 and 15. It should be noted that the TEM samples were prepared by sonicating them in a fluid in order to suspend them. A drop was placed on a TEM grid and the fluid allowed to evaporate. The sonication (high intensity sound) probably breaks up or bends fibers and may cause pieces to agglomerate further.

Figure 16:
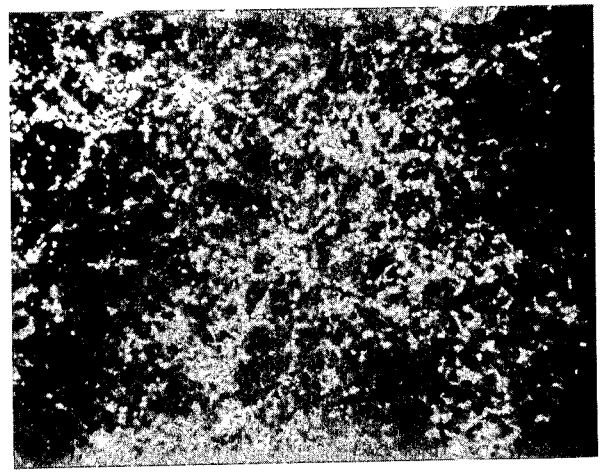
FIG. 16 is a scanning electron micrograph (SEM) at 900 times magnification of Ni fibers in a felt collected in accordance with the present invention in an Earth gravity environment in the presence of an applied magnetic field.
Figure 17:
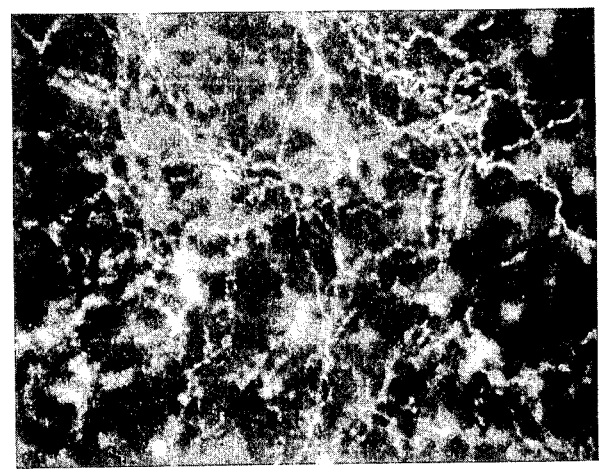
FIG. 17 is a scanning electron micrograph (SEM) at 5,000 times magnification of Ni fibers in a felt collected in accordance with the present invention in an Earth gravity environment in the presence of an applied magnetic field.

The Ni fibers produced with the system of FIG. 6 collected in bundles very similar to the Fe bundles. After a Ni run it was noticed that a transparent Ni "felt" also carpeted the entire surface of the work chamber, an area of 5,000 sq. cm. Pieces of the felt could be lifted up in several sq. cm. areas. FIGS. 16 and 17 are SEM micrographs of the produced Ni felt which show that it is microscopically quite similar in appearance to Fe.

Such "felt" was not noticed in the Fe production runs, but was not specifically looked for.

Figure 18:
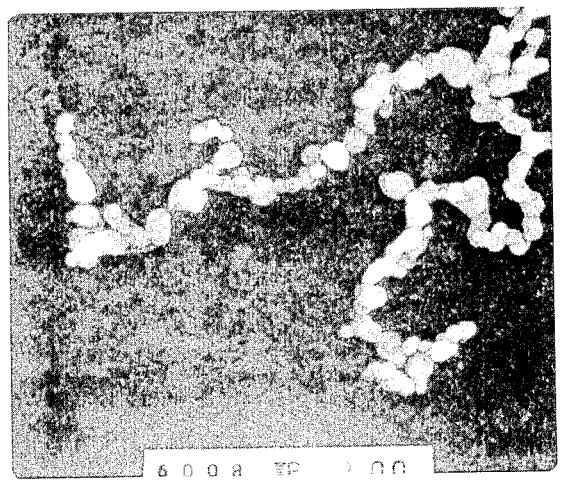
FIG. 18 is a transmission electron micrograph (TEM) at 90,000 times magnification of Ni fibers in a felt collected in accordance with the present invention in an Earth gravity environment in the presence of an applied magnetic field.

The TEM micrograph shown in FIG. 18 reveals a chain of particles forming the fibers, similar to Fe, but with greater fraction of material down to 300 angstroms.

The individual particles in fibers may be single domain particles which develop a net magnetic moment when they cool below their Curie points. The energy of interaction between two magnetic moments, m1 and m2, separated by r is $$U = (u_0/4pi)(m_1 m_2 - 3(m_1 i)(m_2 i))/r^3 \quad (4)$$

where $u_0$ is the permeability of free space and $i$ is a unit vector in the r direction. Here vector dot products are obvious. The lowest energy solution of this equation is when $m_1$ and $m_2$ point in the same direction and along r. Therefore, the system lowers its energy if individual magnetized grains combine into chains or fibers, as observed. Presumably, there would be a tendency for the particles to sinter together if the temperature is high enough when they come into contact.

The transmission electron micrographs of Fe and Ni (FIGS. 15 and 18) do show incomplete sintering of particles. Accordingly, some clumps of fibers were wrapped in Mo foil and sealed in quartz tubes for 10 hour anneals. Two Fe samples were annealed, one at 600 degrees C and one at 900 degrees C. These temperatures were chosen in order to straddle the Fe Curie point of 770 C. A few sq. cm. piece of Ni felt was annealed at 900 degrees C, substantially above the Ni Curie point of 360 degreees C.

One possibility is that the fibers could come apart above their Curie points. The higher temperature annealed samples did break up into smaller pieces than the 600 degree C Fe sample. However, this is thought to be due in part to massive grain growth.

Upon observing a transmission electron micrograph (not shown) of the 900 degree C Fe sample, it was noted that the particles were much larger than in their unannealed state.

It appeared that some particles grew much more than others, as if the growth process proceeded explosively. As is well known, recrystallization and sintering are driven by the lowering of surface energy in the system. It is noteworthy in this context that these materials have a much higher surface to volume ration than is usually present in material being annealed.

Upon observing the transmission electron micrograph (not shown) of the 600 C degree Fe sample, it was noted that much smaller particles were evident, indicating that kinetic factors limit the growth process at these temperatures rather than the available surface energy.

The TEM of the 600 degree C Fe sample also revealed some very straight particles. They have not yet been seen in the unannealed samples. It could be that they are large aspect-ratio single crystal particles which formed during the anneal. If this proves to be the case after more study, then it should be possible to produce conditions of different times, temperatures, gases, catalysts, etc. which favor their growth. Straight, possible single crystalline, particles could ultimately prove to be useful as fine electrodes, probes, or high specific strength dislocation free materials.

It is reasonable to expect that where adjacent fibers touch there will be sintering and that this sintering will produce undesirable large particles. It is convection that produces the tangling of fibers with concomitant interfiber contacts. Therefore, the much less tangled fibers produced in microgravity could yield a much improved annealed product.

Electrostatic particle collection causes particles to form fibers. Ferromagnetic materials can be collected by magnetostatic means, but they are in the form of fibers also. Therefore, the systems of FIGS. 4 and 7 are provided in order to collect particles without causing them to form fibers.

In the system of FIG. 7, a 10 cm. diameter 0.2 micron millipore filter 102 was positioned vertically alongside the charge of source material 111, about 2 cm. from its centerline. The filter 102 was exposed on the source side. The other side was sealed to a separate enclosure with an O-ring. The enclosure was connected to a separate vacuum pump by valves and plumbing in such a way that inert gas and entrained particles would be drained through the filter, as shown in FIG. 7.

Flowrate through the filter with 100 torr of He gas in the work chamber 98 was measured to be $1.8 \times 10^{-3}$ moles per second or 31 torr l/s. The work chamber 98 volume was 40 l.

He gas was admitted to the system through the control valve 110 while the chamber 98 was being evacuated through the filter 102. Pressure was stabilized at 100 torr and Al evaporation commenced. The Al plume was deflected noticeably to the filter 102. The filter 102 quickly became covered with particle deposit.

When the heater 101 was turned off, the filter 102 cleaned the chamber 98 of most of the convecting particles in approximately one minute. The flow lines, as delineated by the suspended particles, disappeared into the filter 102 at a perpendicular angle. This is expected for flow through a filter. The backside of the filter 102 showed no sign of a deposit, indicating a filter efficiency near 100%.

There was no sign of fiber growth in such runs to within a fiber length sensitivity on the order of one mm.

Applications for ultrafine particles include: (a) catalysis, (b) feedstock in solid state chemical reactions, (c) high frequency magnetic devices, (d) dispersion hardening in metals, (e) optical absorbing media, (f) fine sintered filters, (g) new materials, and (h) magnetic drug carriers for cancer therapy.

Applications for ultrafine fibers include: (a) hot wire anemometry, (b) high speed thermocouples, (c) high speed bolometers, (d) fast IR detectors, (e) non-intrusive probes of elecromagnetic fields, (f) electrodes for scanning tunneling studies of surfaces, (g) electrodes for intra-cellular monitoring, (h) cold cathodes, (i) directionally dependent electromagnetic shields, (j) fine sintered filters, (k) composites, (l) acicular magnetic recording media, (m) micro-electrodes for spark erosion machining, (n) exploding wire sources, and (o) fine wires for instrumentation, I.C.'s etc.

The synthesis of new non-equilibrium materials is now felt to be especially important. Generally, the enabling features for non-equilibrium materials synthesis include high specific surface energy and the high quenching rates from the vapor under some conditions. In addition, the opportunity to nucleate new phases may be greater because of the large number of nucleation sites comprised by the ultrafine particles. A new crystal structure for Cr and rapid kinetics for formation of an unusual form of $SiO_2$ in small particles have been reported.

The use of magnetic ultrafine particles for localizing drug delivery in cancer therapy is undergoing tests in laboratory animals. Magnetic particles on the order of 100 angstroms are trapped together with drugs in larger particles of size 0.2 micron to 1 micron. These composite particles are injected into the blood stream. A strong magnet is placed over the site of a tumor and the magnetic field gradient stops the circulating particles in the tumor. The stopped particles release much higher drug doses selectively without killing the experimental animal. Results appear to be quite promising.

Many of the potential uses listed for ultrafine fibers employ the fast thermal response of metallic ultrafine fibers as sensing elements. The thermal response time of a wire of radius r is of the order of $cr^2/k$, where c is the specific heat per unit volume and k is the thermal conductivity. As a typical example, a free standing Al wire of 500 angstrom diameter has a calculated response time of $6 \times 10^{-12}$ sec at room temperature; thus it should be an effective thermal sensor at high frequencies of the order of 160 gigahertz. Below room temperature, its high frequency response should be even greater.

I claim:

1. A system for producing ultrafine particles of a given metallic material, comprising
   means defining a work chanber
   means for providing within the chamber a gas atmosphere that includes inert gas;
   means for evaporating the given material in the gas atmosphere of the work chamber under conditions that cause the evaporated material to condense as ultrafine particles;
   wherein the work chamber is located in a microgravity environment to reduce gravity-caused convection currents in the work chamber that otherwise would promote coalescence of the condensed particles; and
   means for actively collecting the condensed particles by attracting the particles from the gas atmosphere to the collecting means.

2. A system according to claim 1, wherein the collecting means comprise
   means including electrodes for providing an electrostatic field in the work chamber to attract the condensed particles to the electrodes.

3. A system according to claim 2, wherein the electrodes include a pair of opposed conductive plates charged to different potentials.

4. A system according to claim 3, wherein the electrodes further include a charged conductive wire positioned within the portion of the chamber in which the particles condense.

5. A system according to claim 4, wherein the conductive wire is charged to a potential intermediate to the respective potentials of the plates and is positioned adjacent the plates in a plane that is parallel to and between the plates.

6. A system according to claim 2, wherein the electrodes include a charged conductive wire positioned within the portion of the chamber in which the particles condense.

7. A system according to claim 1, wherein the collection means comprise
   means including a magnet for providing a spatially varying magnetic field in the work chamber to attract the condensed particles to the magnet.

8. A system according to claim 1, wherein the collection means comprise
   a filter positioned in the work chamber; and
   means for causing the gas to flow through the filter and carry the condensed particles to the filter and thereby collect on the filter.

9. A system for producing ultrafine particles of a given metallic material, comprising
   means defining a work chamber;
   means for providing within the work chamber a gas atmosphere that includes an inert gas;
   means for evaporating the given material in the gas atmosphere of the work chamber under conditions that cause the evaporated material to condense as ultrafine particles; and
   means for actively collecting the condensed particles by attracting the particles from the gas atmosphere to the collecting means.

10. A system according to claim 9, wherein the collecting means comprise
    means including electrodes for providing an electrostatic field in the work chamber to attract the condensed particles to the electrodes.

11. A system according to claim 10, wherein the electrodes include a pair of opposed conductive plates charged to different potentials.

12. A system according to claim 11, wherein the electrodes further include a charged conductive wire positioned within the portion of the chamber in which the particles condense.

13. A system according to claim 12, wherein the conductive wire is charged to a potential intermediate to the respective potentials of the plates and is positioned adjacent the plates in a plane that is parallel to and between the plates.

14. A system according to claim 10, wherein the electrodes include a charged conductive wire positioned within the portion of the chamber in which the particles condense.

15. A system according to claim 9, wherein the collection means comprise means including a magnet for providing a spatially varying magnetic field in the work chamber to attract the condensed particles to the magnet.

16. A system according to claim 9, wherein the collection means comprise a filter positioned in the work chamber; and means for causing the gas to flow through the filter and carry the condensed particles to the filter and thereby collect on the filter.

17. A system for producing ultrafine fibers of a given nonferromagnetic metallic material, comprising means defining a work chamber;

means for providing within the work chamber a gas atmosphere that includes inert gas;

means for evaporating the given material in the gas atmosphere of the work chamber under conditions that cause the evaporated material to condense as ultrafine particles; and means for collecting the condensed particles in fused chain formations to produce fibers;

wherein the collecting means include electrodes for providing an electrostatic field in the work chamber to attract the condensed particles to the electrodes, to particles attracted to the electrodes and to particles attracted to particles attracted to the electrodes to form the particle chains.

18. A system according to claim 17, wherein the electrodes include a pair of opposed conductive plates charged to different potentials.

19. A system according to claim 18, wherein the electrodes further include a charged conductive wire positioned within the portion of the chamber in which the particles condense.

20. A system according to claim 19, wherein the conductive wire is charged to a potential intermediate to the respective potentials of the plates and is positioned adjacent the plates in a plane that is parallel to and between the plates.

21. A system according to claim 17, wherein the electrodes include a charged conductive wire positioned within the portion of the chamber in which the particles condense.

22. A system according to claim 17, further comprising means for further providing within the gas atmosphere of the work chamber a reactive gas in order to alter the composition of the condensed material.

23. A process for producing ultrafine particles of a given metallic material, comprising the steps of (a) evaporating the given material in a work chamber having a gas atmosphere that includes inert gas under conditions that cause the evaporated material to condense as ultrafine particles;

(b) locating the work chamber in a microgravity environment to reduce gravity-caused convection currents in the work chamber that otherwise would promote coalescence of the condensed particles; and (c) actively collecting the condensed particles by attracting the particles from the gas atmosphere to collecting means.

24. A process according to claim 23, wherein step (c) comprises the step of (d) providing an electrostatic field in the work chamber to attract the condensed particles to predetermined locations in the work chamber.

25. A process according to claim 23, wherein step (c) comprises the step of (d) providing a spatially varying magnetic field in the work chamber to attract the condensed particles to predetermined locations in the work chamber.

26. A process according to claim 23, wherein step (c) comprises the steps of (d) causing the inert gas to flow within the work chamber; and (e) filtering the condensed particles from the flowing inert gas to collect the condensed particles.

27. A process for producing ultrafine particles of a given metallic material, comprising the steps of (a) evaporating the given material in a work chamber having a gas atmosphere that included inert gas under conditions that cause the evaporated material to condense as ultrafine particles; and (b) actively collecting the condensed particles by attracting the particles from the gas atmosphere to collecting means.

28. A process according to claim 27, wherein step (b) comprises the step of (c) providing an electrostatic field in the work chamber to attract the condensed particles to predetermined locations in the work chamber.

29. A process according to claim 27, wherein step (b) comprises the step of (c) providing a spatially varying magnetic field in the work chamber to attract the condensed particles to predetermined locations in the work chamber.

30. A process according to claim 27, wherein step (b) comprises the steps of (c) causing the inert gas to flow within the work chamber; and (d) filtering the condensed particles from the flowing inert gas to collect the condensed particles.

31. A process for producing ultrafine fibers of a given nonferromagnetic metallic material, comprising the steps of (a) evaporating the given material in a work chamber having a gas atmosphere that includes inert gas under conditions that cause the evaporated material to condense as ultrafine particles; and (b) collecting the condensed particles in chain formations to produce fibers by providing an electrostatic field in the work chamber to attract the condensed particles to the electrodes, to particles attracted to the electrodes and to particles attracted to particles attracted to the electrodes to form the particle chains.

32. Ultrafine fibers of a given nonferromagnetic material produced by the process of claim 31.

* * * * *